(12) United States Patent
Auzely-Velty et al.

(10) Patent No.: US 8,377,418 B2
(45) Date of Patent: Feb. 19, 2013

(54) PROCESS FOR PREPARING THERMOSENSITIVE (POLY(ETHYLENE OXIDE) POLY(PROPYLENE OXIDE)) DERIVATIVES THAT CAN BE USED TO FUNCTIONALIZE CHITOSAN

(75) Inventors: Rachel Auzely-Velty, Le Gua (FR); Caroline Creuzet, Gieres (FR)

(73) Assignees: Centre National de la Recherche Scientifique (CNRS), Paris (FR); Universite Joseph Fourier-Grenoble 1, St. Martin d'Heres (FR)

( * ) Notice: Subject to any disclaimer, the term of this patent is extended or adjusted under 35 U.S.C. 154(b) by 334 days.

(21) Appl. No.: 12/677,211

(22) PCT Filed: Sep. 11, 2008

(86) PCT No.: PCT/EP2008/062059
§ 371 (c)(1),
(2), (4) Date: Mar. 9, 2010

(87) PCT Pub. No.: WO2009/034130
PCT Pub. Date: Mar. 19, 2009

(65) Prior Publication Data
US 2010/0204177 A1 Aug. 12, 2010

(30) Foreign Application Priority Data
Sep. 11, 2007 (FR) ...................................... 07 57506

(51) Int. Cl.
- *A61K 51/00* (2006.01)
- *A61K 36/14* (2006.01)
- *A61K 9/22* (2006.01)
- *C08B 37/08* (2006.01)

(52) U.S. Cl. ......... 424/1.73; 424/1.65; 424/468; 536/20
(58) Field of Classification Search .................. 424/1.73, 424/1.65, 468; 536/20
See application file for complete search history.

(56) References Cited

U.S. PATENT DOCUMENTS
| | | | |
|---|---|---|---|
| 5,990,237 A | 11/1999 | Bentley et al. | |
| 2003/0129730 A1 | 7/2003 | Chenite et al. | |
| 2004/0166158 A1 | 8/2004 | Davis et al. | |

FOREIGN PATENT DOCUMENTS
| | | |
|---|---|---|
| WO | 03049699 A | 6/2003 |
| WO | WO 03/049699 A2 | 6/2003 |

OTHER PUBLICATIONS

International Search Report dated Oct. 17, 2008 concerning PCT/EP2008/062059.
International Search Report issued in application No. PCT/EP2008/062059 on Oct. 27, 2008.
Bhattarai et al., "PEG-grafted chitosan as an injectable thermosensitive hydrogel for sustained protein release," Journal of Controlled Release, vol. 103, pp. 609-624, 2005.
Hoffman et al., "Graft Polymers of PEO-PPO-PEO Triblock Polyethers on Bioadhesive Polymer Backbones: Synthesis and Properties," American Chemical Society, vol. 38, No. 1, pp. 524-525, 1997.
Creuzet et al., "Synthèse et etude d'hydrogels thermosensibles obtenus par modification cheimique controlee du chitosane," L'Actualité Chimique, vol. 294, pp. 34-38, 2006.
Bhattarai et al., "PEG-grafted chitosan as an injectable thermosensitive hydrogel for sustained protein release," J. Controlled Release, 2005, pp. 609-624, vol. 103.
Chenite et al., "Novel injectable neutral solutions of chitosan form biodegradable gels in situ," Biomaterials, 2000, pp. 2155-2161, vol. 21.
Cho et al., "Chondrogenic differentiation of human mesenchymal stem cells using a thermosensitive poly(N-isopropylacrylamide) and water-soluble chitosan copolymer," Biomaterials, 2004, pp. 5743-5751, vol. 25.
Chung et al., "Synthesis and characterization of Pluronic® grafted chitosan copolymer as a novel injectable biomaterial," Current Applied Physics, 2005, pp. 485-488, vol. 5.
Harris et al., "Synthesis and Characterization of Poly(ethylene Glycol) Derivatives," J. Polymer Science: Polymer Chemistry Edition, 1984, pp. 341-352, vol. 22.
Yu et al., "Anionic Copolymerisation of Ethylene Oxide and Propylene Oxide. Investigation of Double-Bond Content by NMR Spectroscopy," Eur. Polym. J., 1995, pp. 589-593, vol. 31, No. 6.

*Primary Examiner* — Scarlett Goon
(74) *Attorney, Agent, or Firm* — Foley & Lardner LLP (57) ABSTRACT

The invention relates to a thermosensitive (poly(ethylene oxide) poly(propylene oxide))-acetal derivative, which can be used to functionalize chitosan, and to the process for the preparation thereof. The invention therefore also relates to a process for functionalizing chitosan by grafting this thermosensitive copolymer and optionally another thermosensitive polymer, poly(ethylene oxide). A subject of the invention is also a chitosan-(poly(ethylene oxide) poly(propylene oxide))-poly(ethylene oxide) derivative which has the advantage of being water-soluble at physiological pH. The invention therefore also relates to the aqueous compositions comprising this derivative and to the use of this composition for the manufacture of gel by heating.

26 Claims, 4 Drawing Sheets

PROCESS FOR PREPARING THERMOSENSITIVE (POLY(ETHYLENE OXIDE) POLY(PROPYLENE OXIDE)) DERIVATIVES THAT CAN BE USED TO FUNCTIONALIZE CHITOSAN

The invention relates to novel thermosensitive polymers, which notably be used in the synthesis of chitosan derivatives.

Reversible hydrogels formed in situ following an increase in temperature presently arouse increasing interest because of their many potential applications in the cosmetics, pharmaceutical and biomedical fields. In these systems, the formation of the physical junctions required for gelling is generally due to the combination of polymers having a lower critical temperature for demixing. These so-called LCST (Lower Critical Solution Temperature) polymers lead to phase separation when the temperature becomes greater than LCST. Indeed, these systems have their hydrophobicity increasing with temperature. As examples, mention may be made of poly(N-isopropylacrylamide) (PNIPAM) and triblock polyethers of poly(ethylene oxide) (PEO) and of poly(propylene oxide) (PPO) marketed under the name of Pluronics® (BASF) or Poloxamers® (ICI) (Gil et al., 2004). Triblock polymers PEO-PPO-PEO have the property of forming gels at high temperature; now for this, they require being at very high concentrations in solution (from 200 to 300 g/L), which does not form optimum conditions for biocompatibility. One of the possible strategies for overcoming this problem is based on low level grafting of these polymers on a biopolymer, such as chitosan. This approach has several advantages; a thermogelling behavior may be observed in an aqueous medium with low polymer concentrations (10 g/L), moreover combining the properties of biocompatibility, biodegradability and biological properties of chitosan. This polysaccharide of natural origin increases the healing rate of open wounds, while stimulating the immune response and reconstruction of the tissues, while preventing microbial infections and absorbing the exudates. It also proves to be a good substrate for cell culture and further stimulates cell growth. These properties therefore make it a good candidate for healing wounds, regenerative medicine (bone reconstruction) and the elaboration of drug administration systems (implants, solutions, hydrogels, patches).

In this context, the inventors have developed thermogelling systems by grafting LCST polymers on chitosan. These systems consist in aqueous solutions for which the pH advantageously varies from 4 to physiological pH values, leading to transparent gels by heating.

Few studies have been dedicated to developing thermoreversible hydrogels based on natural polymers. Chemte et al. (Biomaterials (2000), 21, 2155-2161) have shown the possibility of obtained thermogelling systems from aqueous solutions with a physiological pH of chitosan and of salts of glycerol-2-phosphate. However, obtaining these gels requires the use of a large amount of salts which does not allow their use in certain biomedical applications. Derivatives of chitosan bearing PNIPAM chains have also been developed with the purpose of using them in tissue engineering (Cho et al. Biomaterials (2004), 25, 5743-5751). However, PNIPAM does not exhibit the biocompatibility characteristics required for real applications in vivo. Chung et al. (Curr. Applied Phys. (2005), 5, 485-488) have described the synthesis of biocompatible thermo-thickening chitosan derivatives bearing chains of the Pluronics® type. But the bifunctional nature of such chains makes the control of the synthesis relatively difficult.

Poly(ethylene oxide) poly(propylene oxide), PEOPPO, commercially called Jeffamine® (Huntsman), is a copolymer with a random arrangement of ethylene oxide and propylene oxide units from the family of Pluronics®. This biocompatible copolymer had been used by L'Alloret (FR 2 811 995) for preparing thermogelling grafted copolymers derived from synthetic polymers or from derivatives of polysaccharides other than chitosan (cellulose and derivatives, galactomannans, alginates). This polymer was also used for functionalizing chitosan. Chitosan has an amine function in position C-2, allowing regioselective reactions to be carried out. The synthesis of chitosan-PEOPPO is based on the functionalization of PEOPPO by a reducing sugar in a first step (a coupling reaction of the peptide type between PEOPPO and protected galacturonic acid followed by deprotection of the hydroxyls of the sugar, leading to the PEOPPO-GA derivative), followed in a second step for the coupling of modified PEOPPO with chitosan by a reducing amination reaction. The carbon C-1 of the sugar, because of its hemiacetal nature, may react with the amine function of chitosan (Creuzet et al., l'actualite chimique (2006), 294, 34-38). However, with this method it is not possible to produce large (industrial) amounts of modified polysaccharide; the PEOPPO-GA derivative having a synthesis which is difficult to apply and is costly.

The inventors thus developed a novel synthesis method via a novel derivative, PEOPPO-acetal, in order to lead to CHI-PEOPPO derivatives with a variable degree of substitution (DS), advantageously soluble in an aqueous medium at pH 4 and thermogelling. The sol-gel transition temperature depends on the degree of substitution, so that the properties may be adjusted depending on the desired applications. In order to broaden the applications, CHI-PEOPPO-PEO derivatives, advantageously soluble in an aqueous medium at physiological pH values, were moreover developed from the PEOPPO-acetal intermediate or from the CHI-PEOPPO derivative.

Therefore the first object of the invention is a method for preparing a thermosensitive PEOPPO-acetal derivative, comprising the following successive steps:

a. reacting one or more random polyetheramines (PEOPPO) of generic formula (I)

wherein p represents an integer varying from 1 to 40, advantageously from 3 to 29, and m represents an integer varying from 1 to 40, advantageously from 1 to 31,
with succinic anhydride in order to lead to the corresponding acid;

b. coupling the acid obtained following step a) with 2,2-dimethoxyethylamine in order to lead to the sought PEOPPO-acetal derivative.

Within the scope of the present invention, the abbreviations PEOPPO refer to one or more random copolymers of ethylene oxide and of propylene oxide. Within the scope of the method according to the invention, it is possible to use either a single random copolymer or ethylene oxide and of propylene oxide, or a mixture of different random copolymers of ethylene oxide and propylene oxide, said copolymers may notably differ by the propylene oxide/ethylene oxide ratio and the molecular weight.

The random polyetheramines used within the scope of the present invention are advantageously copolymers marketed by Huntsman under the trade name of Jeffamine®, in particular the random copolymers:
- with an approximate molecular mass of 600 g/mol, the propylene oxide/ethylene oxide ratio being 9/1;
- with an approximate molecular mass of 1,000 g/mol, the propylene oxide/ethylene oxide ratio being 3/19;
- with an approximate molecular mass of 2,000 g/mol, the propylene oxide/ethylene oxide ratio being 29/6; and
- with an approximate molecular mass of 2,000 g/mol, the propylene oxide/ethylene oxide ratio being 10/31.

In addition to the products available commercially, the random polyetheramines may be easily prepared by conventional methods well-known to one skilled in the art (Y. Deng, J. Ding, G. Yu, R. H. Mobbs, F. Heatley, C. Price, C. Booth, Plmer. (1992), 33, 1959-1962; G.-E. Yu, F. Heatley, C. Booth, T. G. Blease, Eur. Polym. J. (1995), 31, 589-593).

It is known that the random distribution of the ethylene oxide and propylene oxide units is expressed by the existence of a critical lower temperature of demixing, beyond which separation of macroscopic phases is observed.

Within the scope of the invention, the expression "thermosensitive derivative" refers to a polymer with LOST, i.e. a polymer for which the solubility in water is modified beyond a certain temperature. These are polymers having a demixing temperature by heating (or cloud point) defining their solubility zone in water. The minimum demixing temperature obtained depending on the polymer concentration is called LOST. For each polymer concentration, this demixing temperature by heating is observed; it is higher than LOST which is the minimum point of the curve. Below this temperature, the polymer is soluble in water; above this temperature the polymer loses its solubility in water.

By soluble in water, it is meant that the units have a solubility at 20° C., of at least 1 g/L, preferably at least 2 g/L.

Measurement of LOST may be conducted visually: the temperature at which the cloud point of the aqueous solution appears is determined; the cloud point is expressed by opacification of the solution or loss of transparency.

Generally, a transparent composition will have a maximum light transmittance value, regardless of the wavelength comprised between 400 and 800 nm, through a sample with a thickness of 1 cm, of at least 80%, preferably of at least 90% (see EP291334). The transmittance may be measured by placing a sample with a thickness of 1 cm in the light ray of a spectrophotometer operating in the wavelength of the light spectrum.

The method is advantageously carried out at least partly under anhydrous conditions, in order to ensure good yields. As a particularly suitable solvent example for conducting the step a), mention may be made of dimethylformamide (DMF), in particular anhydrous DMF.

In a preferred embodiment of the invention, to a solution of PEOPPO in DMF, advantageously anhydrous DMF, is added succinic anhydride in solution in DMF, advantageously anhydrous DMF. The (anhydrous) PEOPPO/DMF solution is advantageously maintained under an inert atmosphere, such as under nitrogen. The required molar amount of succinic anhydride is at least the molar amount of PEOPPO; advantageously the succinic anhydride is introduced in slight excess (advantageously 1.05 molar equivalents).

The solvent used in step b) is also advantageously DMF, in particular anhydrous DMF.

In step b), the coupling reaction is advantageously carried out in the presence of 1-ethyl-3-[3-(dimethylamino)propyl]-carbodiimide and of diisopropylethylamine (or triethylamine). This step b) advantageously comprises the successive addition
- of 1-ethyl-3-[3-(dimethylamino)propyl]-carbo-diimide and of diisopropylethylamine (or triethylamine), solubilized in anhydrous DMF, and then
- 2,2-dimethoxyethylamine.

It is also possible to add beforehand N-hydroxybenzotriazole. Step b) then advantageously comprises the successive addition
- of N-hydroxybenzotriazole, and then
- of 1-ethyl-3-[3-(dimethylamino)propyl]-carbodiimide and of diisopropylethylamine (or triethylamine), solubilized in anhydrous DMF, and then
- 2,2-dimethoxyethylamine.

With the method according to the invention, steps a) and b) may be carried "in a single pot", i.e. in a single and same reactor, without any intermediate step for isolating the obtained compound following step a). Steps a) and b) are therefore advantageously carried out "in a single pot".

In order to make sure that before the coupling reaction, the reaction of PEOPPO with succinic anhydride is completed, the reaction medium is left under stirring for the time required for this. The reaction medium may thus be left under stirring at room temperature and at atmospheric pressure. At the scale of the laboratory (<500 mL), the reaction medium is advantageously left under stirring at room temperature and at atmospheric pressure for 5 hours.

Following step b) the reaction medium is advantageously left under stirring at room temperature and at atmospheric pressure for the time required for making sure that the coupling reaction is completed, which is checked at the scale of the laboratory (<500 mL) by leaving the solution under stirring overnight.

In order to recover the PEOPPO-acetal, it is advantageously possible to proceed in the following way. The solvent (DMF) is evaporated and the product is taken up in a suitable solvent such as dichloromethane. The organic phase is successively washed with slightly acid water (pH 4), and then with water. The organic phase is dried, for example by drying on sodium sulfate, and then evaporated in order to obtain the acetal derivative.

With the method according to the invention it is possible to obtain the PEOPPO-acetal derivative with yields above 80%.

In an alternative of the invention, in step a), a single random polyetheramine is reacted. In another alternative of the invention, in step a), at least two different random polyetheramines are reacted.

The second object of the invention is a PEOPPO-acetal derivative obtained by the method, the PEOPPO abbreviations designating the random copolymers of ethylene oxide and propylene oxide, either identical or different, as defined earlier.

The third object of the invention is a method for the synthesis of grafted chitosan comprising (i) a step for hydrolyzing the PEOPPO-acetal derivative according to the invention into a PEOPPO-CHO derivative (i.e. into the corresponding aldehyde) followed (ii) by a step for grafting said PEOPPO-CHO derivative on chitosan or on one of its derivatives by a reaction of the reducing amination type.

The first step (i) consists of deprotecting the aldehyde function of the PEOPPO-acetal, to do this, at the scale of the laboratory (<500 mL), the latter is advantageously solubilized in a trifluoroacetic acid/water (TFA/$H_2O$) mixture, for example in proportions (4/1) (v/v). The reaction medium may be left under stirring overnight at room temperature and at atmospheric pressure. After evaporation of the TFA/H$_2$O mixture, the obtained aldehyde may be solubilized in a ethanol/water mixture (in particular EtOH/H$_2$O (1/1) (v/v)) and the pH of the solution is advantageously adjusted to pH 5.1.

The aldehyde is then added to the chitosan, which may be solubilized beforehand in a CH$_3$COOH/EtOH (3:2 v/v) mixture for example. The pH of the mixture is then adjusted to 5.1. An aqueous solution of a reducing agent, such as an aqueous solution of sodium cyanoborohydride or of picoline borane (PicBH$_3$) or sodium borohydride is advantageously added. The reaction medium may be left under stirring for the necessary time, 24 hours at the scale of the laboratory (<500 mL), at room temperature and at atmospheric pressure. The expected product may be recovered by precipitation, by adjusting the pH of the reaction medium to 9. The latter is then washed, filtered and dried.

Chitosan or one of its derivatives advantageously fits the following formula (II):

(II)

wherein n varies from 60 to 6,000 and R represents
a hydrogen atom H,
an acetyl radical COCH$_3$, the acetylation degree being advantageously comprised between 0 and 0.5, more advantageously between 0 and 0.2.

The inventors have noticed that the degree of substitution of PEOPPO on the chitosan, DS$_1$, is adjustable depending on the reaction conditions used and, in particular, depends on the aldehyde concentration (PEOPPO-CHO). Table 1 groups the reaction conditions used for the synthesis of different samples of CHI-PEOPPO with variable DS$_1$; random polyetheramine having an approximate molecular mass of 2,000 g/mol, the propylene oxide/ethylene oxide ratio being 29/6.

TABLE 1

Reaction conditions used for the synthesis of CHI-PEOPPO derivatives with variable DS$_1$.

| Reaction | NaCNBH$_3$[a] | PEOPPO-CHO[a] | Yield (%) | DS$_1$[b] |
|---|---|---|---|---|
| 1 | 1.2 | 0.05 | 72 | 0.04 |
| 2 | 1.2 | 0.1 | 63 | 0.1 |
| 3 | 1.2 | 0.2 | 48 | 0.17 |

[a]Number of molar equivalents/recurrent unit mol;
[b]obtained by $^1$H NMR

The data of Table 1 show that the grafting reaction is perfectly controlled. The result thereof is a family of products with variable DS$_1$, which allows adjustment of the relevant temperature range for the contemplated application. In the case of the tested PEOPPO derivative (a relatively hydrophobic polymer rapidly combined together by heating), it is seen that the higher the degree of substitution DS$_1$, the lower the transition temperature. Thus, for values of DS$_1$=0.04, the transition temperature is located around 40° C. while for values of DS$_1$=0.17, the transition temperature is located around 25° C.

The degree of substitution of PEOPPO on chitosan is advantageously comprised between 0.02 and 0.3, more advantageously between 0.05 and 0.2.

The CHI-PEOPPO derivatives obtained by this method have interesting thermogelling properties, i.e. when they are put into a solution, a reversible and controllable sol-gel transition is obtained. Further they are soluble in water at pHs close to 4 (±1). The CHI-PEOPPO chitosan derivatives may be solubilized in aqueous compositions (pH of 4±1), for example in an amount comprised between 2 and 30 g/L, which may moreover comprise a cosmetically or pharmaceutically acceptable medium. The resulting aqueous solutions lead to highly viscous liquids or to transparent gels by heating. These bioresorbable systems may be used in cosmetic, pharmaceutical or biomedical formulations which may be transparent for modifying the flow properties thereof depending on the temperature. The gelling capacity of the aqueous solutions comprising CHI-PEOPPO derivatives at temperatures close to those of the human body may give the possibility of avoiding surgeries, these gels then been able to be injected or applied to specific sites. These thermogels further have the advantage of being bioresorbable. These aqueous solutions may therefore be used as an injectable hydrogel in therapeutic or cosmetic applications.

In order to broaden applications, thermogelling CHI-PEOPPO-PEO derivatives soluble in an aqueous medium at physiological pH values were developed from the obtained intermediate PEOPPO-acetal or CHI-PEOPPO derivative. These derivatives are characterized by the presence, in addition to PEOPPO chains, of poly(ethylene oxide) (PEO) chains directly grafted on chitosan, which impart to the chitosan, solubility properties in water at a neutral pH. Bhattarai et al. (Macromol. Biosci. (2005), 5, 107-11 and J. Controlled Release (2005), 103, 609-624) have shown that the introduction of a PEO chain on chitosan may lead to thermoassociative behavior if the DS is not too high (DS~0.07-0.1). For DSes greater than 0.1, the CHI-PEO derivatives are soluble in water but no longer exhibit any thermothickening effect. The inventors have noticed that with the synthesis of CHI-PEO derivatives with DS<0.1, it is not possible to obtain perfect solubility of the polymers in water. Moreover, the increase in the viscosity of the solutions of CHI-PEO derivatives with DS~0.07-0.1 described by Bhattarai et al., remains moderate (an increase by a factor of 6 for a 30 g/L aqueous solution). On the contrary, the CHI-PEOPPO-PEO derivatives according to the invention allow much higher viscosity gains.

The method for synthesis of grafted chitosan therefore advantageously comprises an additional step (iii) for functionalizing the obtained CHI-PEOPPO chitosan derivative following step (ii) by a polymer, in particular a poly(ethylene oxide) (PEO). The PEO may have a molecular mass comprised between 1,000 and 5,000 g/mol. The degree of substitution of PEO on chitosan, DS$_2$, should be greater than 0.1 in order to obtain perfect solubility of the derivatives in water. The degree of substitution of the PEO on chitosan, DS$_2$ is advantageously comprised between 0.1 and 0.5, more advantageously between 0.1 and 0.3.

According to an alternative of the invention, a monoaldehyde derivative of PEO is prepared first. For this, a solution of Dess-Martin Periodinane (DMP) in a solvent such as DMSO, may be slowly added to a solution of poly(ethylene oxide) methyl monoether in a suitable solvent such as a solution of anhydrous CH$_2$Cl$_2$/dimethylsulfoxide (DMSO) (97/3 (v/v)), under nitrogen. The reaction medium may be left under stirring, for example for 2 hours on the scale of the laboratory (<500 mL) at room temperature. The medium is then concentrated, the product precipitated, isolated and dried.

To a solution of chitosan-PEOPPO, which may be solubilized beforehand in a $CH_3COOH/EtOH$ (3/2 (v/v)) mixture, is added an aqueous solution containing the PEO monoaldehyde derivative. The pH of the mixture is then adjusted to 5.1. An aqueous solution of sodium cyanoborohydride or picoline borane or sodium borohydride (reducing agents) may be added. The pH of the reaction medium is adjusted to 9 and then the CHI-PEOPPO-PEO derivative is purified and isolated.

According to another alternative of the invention, the CHI-PEOPPO-PEO derivative may be obtained by a method comprising the following successive steps:
  a'. Preparation of a CHI-PEO chitosan derivative from native chitosan by grafting a polyethylene oxide) chain, said chain advantageously having a molecular mass comprised between 1,000 and 5,000 g/mol; said CHI-PEO derivative should have a degree of substitution greater than 0.1;
  b'. Reaction of the CHI-PEO derivative obtained in step a) with the PEOPPO-acetal derivative according to the invention hydrolyzed beforehand in order to lead to the sought derivative.

The native chitosan may first of all be modified with a PEO aldehyde derivative, obtained by oxidation with the Dess-Martin reagent (Dess-Martin periodinane (DMP)) of the corresponding commercial alcohol, leading to the formation of a Schiff base. The latter may be reduced in a homogeneous aqueous medium in the presence of a reducing agent (picoline borane ($PicBH_3$) or sodium borocyanohydride ($NaCNBH_3$) or sodium borohydride ($NaBH_4$)) in order to lead to a CHI-PEO derivative, soluble in water at neutral pH. The latter is purified, for example by ultrafiltration. The introduction of PEOPPO chains on the preceding derivative, by the same method as the one described earlier (grafting of PEOPPO on chitosan) leads to the expected product. Additionally via oxidation of PEO-OH by the Dess-Martin reagent, the aldehyde derivatives of PEO may be prepared by other methods well-known to one skilled in the art, such as for example an oxidation in the presence of acetic acid and DMSO(N. Bhattarai, H. R. Ramay, J. Gunn, F. A. Matsen, M. Zhang, J. Controlled Release 103 (2005), 609-624) and J. M. Harris, E. C. Struck, M. G. Case, M. S. Paley, J. M. Vanalstine, D. E. Brooks, J. Polym. Part A.: Polym. Chem. 22 (1984), 341-352).

The first alternative consisting of grafting PEO directly on the CHI-PEOPPO derivative has the advantage of being simpler to apply for purifying the final product.

The fourth object of the invention is a CHI-PEOPPO-PEO chitosan derivative which may be obtained by the method according to the invention.

The invention also relates to an aqueous composition comprising at least one CHI-PEOPPO-PEO chitosan derivative according to the invention and an aqueous phase. The CHI-PEOPPO-PEO chitosan derivative is advantageously present in an amount comprised between 2 and 30 g/L. The pH of said aqueous composition advantageously varies from 4 to a physiological pH, preferably the pH is close to the physiological pH (physiological pH ±1), the CHI-PEOPPO-PEO chitosan derivative having the advantage of being soluble in water at the physiological pH. The aqueous composition according to the invention may moreover comprise a cosmetically or pharmaceutically acceptable medium.

Another object of the invention is the use of the aqueous composition according to the invention for making gels by heating.

The CHI-PEOPPO-PEO derivatives have, as for the CHI-PEOPPO derivatives interesting thermogelling properties, i.e. when they are put into solution a reversible and controllable sol-gel transition is obtained. The resulting aqueous solutions lead to highly viscous liquids or to transparent gels by heating, in particular to a temperature which may be close to that of the human body. Further, these derivatives have the advantage of being soluble in water at the physiological pH facilitating their biomedical applications. These bioresorbable systems may thus be used in cosmetic, pharmaceutical or biomedical formulations, which may be transparent, in order to modify the flow properties thereof depending on the temperature. In particular, they may be used for making injectable hydrogels.

This family of thermogelling derivatives of chitosan, soluble in a aqueous medium, for which the pH varies from 4 to physiological pH values, is able to find various applications in the cosmetic, pharmaceutical or biomedical fields.

The following examples illustrate the invention but are not limiting. In these examples, the polymer concentration is expressed in g/L or in monomol/L, corresponding to the number of moles of recurrent units in 1 L of solution.

EXAMPLE 1

Synthesis of a PEOPPO-Acetal Derivative

To a solution of PEOPPO (7.01 g, 3.2 mmol) in anhydrous DMF (300 mL) under nitrogen, succinic anhydride (0.336 g, 3.36 mmol) in solution in anhydrous DMF (20 mL) is added. The reaction medium is left under stirring at room temperature (and at atmospheric pressure) for 5 hours. Are then added successively, N-hydroxybenzotriazole (HOBt) (0.432 g, 3.2 mmol) solubilized in anhydrous DMF (10 mL), 1-ethyl-3-[3-(dimethylamino)propyl]-carbodiimide (EDC) (0.675 g, 3.52 mmol) and diisopropylethylamine (DIEA) (0.600 mL, 3.52 mmol) solubilized together in anhydrous DMF (10 mL) and finally 2,2-dimethoxyethylamine (0.47 g, 4.48 mmol). The reaction medium is left under vigorous stirring overnight at room temperature and at atmospheric pressure. After evaporation of DMF, the product is taken up with dichloromethane. The organic phase is successively washed with slightly acid water (pH 4), and then with water. The organic phase is dried on sodium sulfate, and then evaporated in order to obtain the expected acetal derivative with a yield of 86%.

EXAMPLE 2

Synthesis of a CHI-PEOPPO Derivative with a DS of 0.1

(addition of 0.11 molar equivalent of PEOPPO relatively to the chitosan). The first step consists of deprotecting the aldehyde function of PEOPPO-acetal. The latter (1.8 g, 0.66 mmol) is solubilized in a $TFA/H_2O$ mixture (23 mL) in the proportions (4/1) (v/v). The reaction medium is left under vigorous stirring for one night at room temperature and at atmospheric pressure. The $TFA/H_2O$ mixture is evaporated in the rotary evaporator (Rotavapor). The thereby obtained aldehyde (0.66 mmol) is solubilized in an $ETOH/H_2O$ mixture (1/1 (v/v), 15 mL) and the pH of the solution is adjusted to pH 5.1. The latter is then added to the chitosan (1 g, 6 mmol), solubilized beforehand in a $CH_3COOH$ 0.2 M/EtOH mixture (3:2 (v/v), 320 mL). The pH of the mixture is then adjusted to 5.1 with a sodium hydroxide (0.5 M) solution. An aqueous solution (2 mL) of sodium cyanoborohydride (0.532 g, 7.2 mmol) is added. After 24 hours of stirring at room temperature and at atmospheric pressure, the pH of the reaction medium is adjusted to 9 leading to precipitation of the expected product. The latter is then successively washed with EtOH/H$_2$O mixtures (3/2, 7/3, 4/1, 9/1 (v/v)) and then with ethanol. The product is filtered on a frit 4 and dried in the open air. 1.6 g of CHI-PEOPPO derivative is obtained (63% yield). The degree of substitution (as determined by $^1$H NMR at 25° C.) of the derivative is 0.1.

EXAMPLE 3

Synthesis of a CHI-PEOPPO-PEO Derivative

A synthesis carried out with a PEO of molar mass 2,000 g/mol, a CHI-PEOPPO with DS 0.1 and a PEO DS of ~0.25 is targeted.

To a solution of poly(ethylene oxide) methyl monoether (2 g, 1 mmol) in a solution of anhydrous CH$_2$Cl$_2$/DMSO (97/3 (v/v), 100 mL) under nitrogen is slowly added a solution of Dess-Martin Periodinane (DMP) (0.424 g, 1 mmol) in DMSO (4 mL). The reaction medium is left under stirring for 2 hours at room temperature. The medium is concentrated with the rotary evaporator until a whitish oil is obtained. The residual oil precipitates from ethyl ether (600 mL).

The raw product is isolated by filtration on a frit 4. The PEO monoaldehyde derivative obtained after filtration is dried under reduced pressure at 25° C. for 2 hours.

To a solution of chitosan-PEOPPO with DS 0.1 (0.3 g; 0.75 mmol) solubilized beforehand in a CH$_3$COOH 0.2 M/EtOH mixture (3/2 (v/v), 80 mL), is added an aqueous solution of oxidized PEO (0.52 g, 0.26 mmol). The pH of the mixture is then adjusted to 5.1 with a sodium hydroxide (0.5 M) solution. An aqueous solution (2 mL) of sodium cyanoborohydride (0.028 g, 0.375 mmol) is added. After 24 hours of stirring at room temperature and at atmospheric pressure, the pH of the reaction medium is adjusted to 9. The product, which does not precipitate, is then purified by ultrafiltration by using H$_2$O as a washing solvent (and a membrane Millipore YM minimum 10, preferentially 30 or 100). After freeze-drying, the CHI-PEOPPO-PEO derivative is obtained (66% yield).

EXAMPLE 4

Flow Behavior of CHI-PEOPPO Derivatives in an Aqueous Medium

It was checked that the aqueous solutions comprising the CHI-PEOPPO derivatives at a concentration of 10 g/L (0.024 monomol/L) in AcOH 0.3 M/AcONa 0.05 M, have a sol-gel transition which is reversible.

Figure 1:
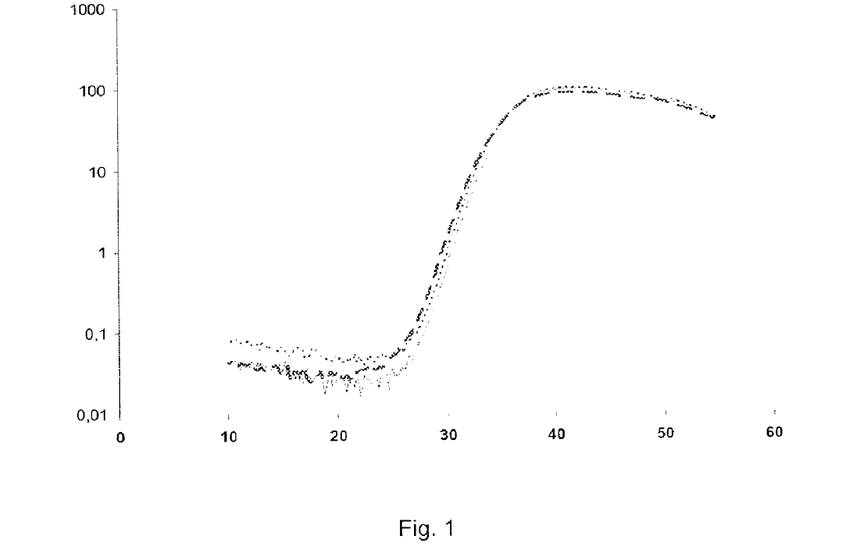

The results are given in FIG. 1 which shows the time course of the viscosity (Pa·s) of the aqueous solution versus temperature (° C.). Caption:
  Forward 1: dotted line ( . . . )
  Backward 1: solid line (—)
  Forward 2: dashed line ( - - - )

It is therefore seen that the sol-gel transition is reversible and reproducible.

EXAMPLE 5

Flow Behavior of CHI-PEOPPO-PEO Derivatives in an Aqueous Medium

Figure 2:
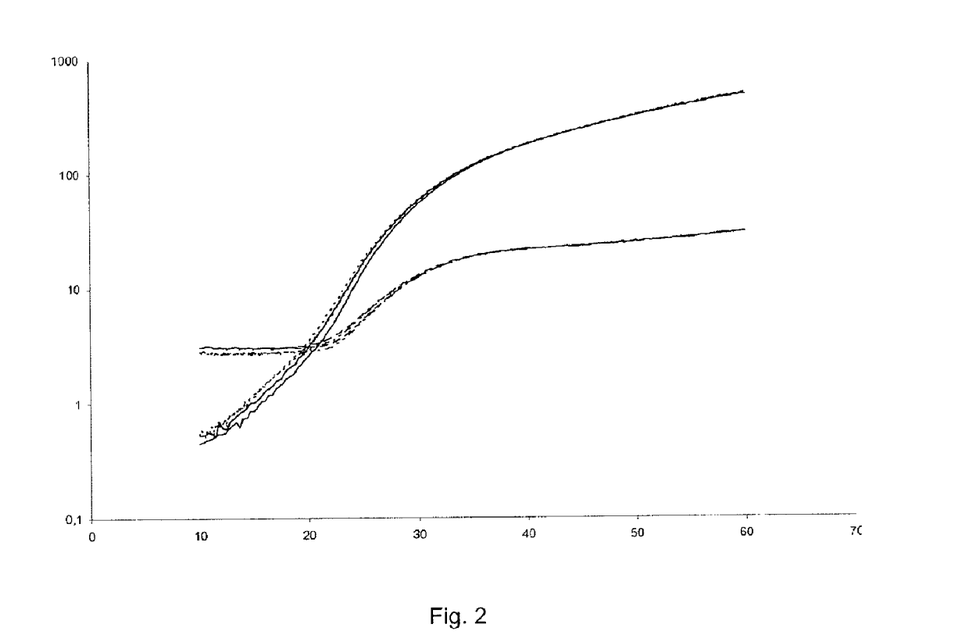

FIG. 2 shows the reversible sol-gel transition of the CHI-PEOPPO-PEO derivative (DS$_2$=0.26, DS$_1$=0.17) soluble in an aqueous medium at a neutral pH. The plotted curves give the variation of the preservation (elastic) G' and loss (viscous) G" (Pa) moduli versus temperature (° C.) for the thermoassociative copolymer based on CHI-PEOPPO-PEO chitosan, under the following operating conditions: frequency set to 1 Hz; heating rate: 1° C./min; solvent: NaCl 0.1 M; Cp=40 g/L (0.035 monomol/L) during the first heating and during a second heating.
  Caption of FIG. 2:
  G', forward 1: dotted line ( . . . )
  G", backward 1: dash-dot line (-.-.-.)
  G', forward 2: solid line (—)
  G", forward 2: dashed line ( - - - )

It is therefore seen that the sol-gel transition is reproducible.

EXAMPLE 6

Flow Behaviour of CHI-PEOPPO and CHI-PEOPPO-PEO Derivatives in an Aqueous Medium, Depending on Temperature Demonstration of the Thermogelling Nature Rheological measurements and conditions of flow and of dynamic flow have allowed clear demonstration of the thermoassociative behaviour of CHI-PEOPPO and CHI-PEOPPO-PEO derivatives.

Figure 3:
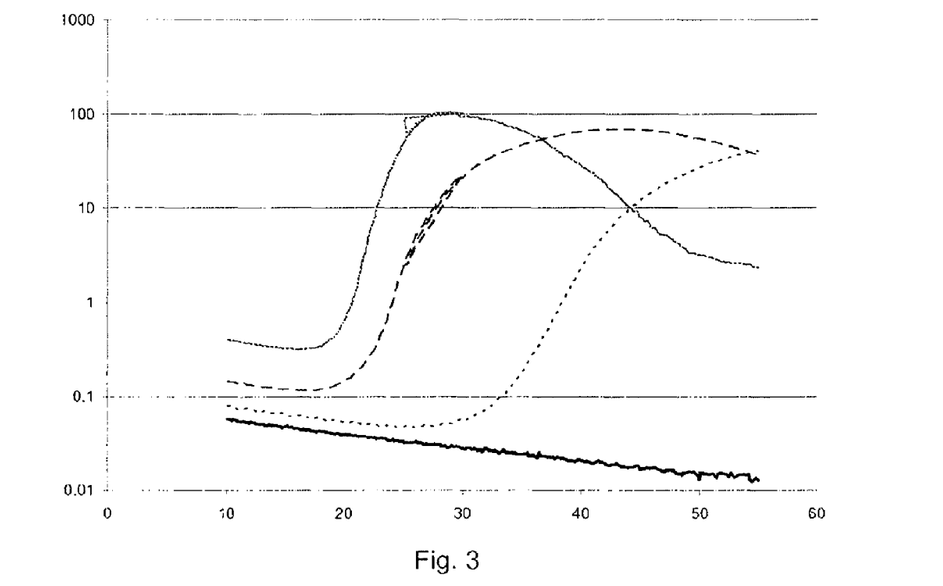

FIG. 3 shows the change in viscosity versus temperature measured from a solution of CHI-PEOPPO derivatives with variable DS$_1$ under the following operating conditions: shear rate: 1 s$^{-1}$; heating rate: 1° C./min; solvent: acetic acid (AcOH) 0.3 M/sodium acetate (AcONa) 0.05 M; polymer concentration=Cp=0.024 monomol/L. The plotted curves give the change in viscosity (Pa·s) versus temperature (° C.). Caption if FIG. 3:
  CHI-PEOPPO DS$_1$=0.17: solid line (—)
  CHI-PEOPPO DS$_1$=0.1: dashed line ( - - - )
  CHI-PEOPPO DS$_1$=0.04: dotted line ( . . . )
  CHI: bold solid line (━━)

A remarkable increase in the viscosity by a factor comprised between 100 and 1,000 depending on DS$_1$ is reported. The transition temperature is closely related to DS$_1$.

Figure 4:
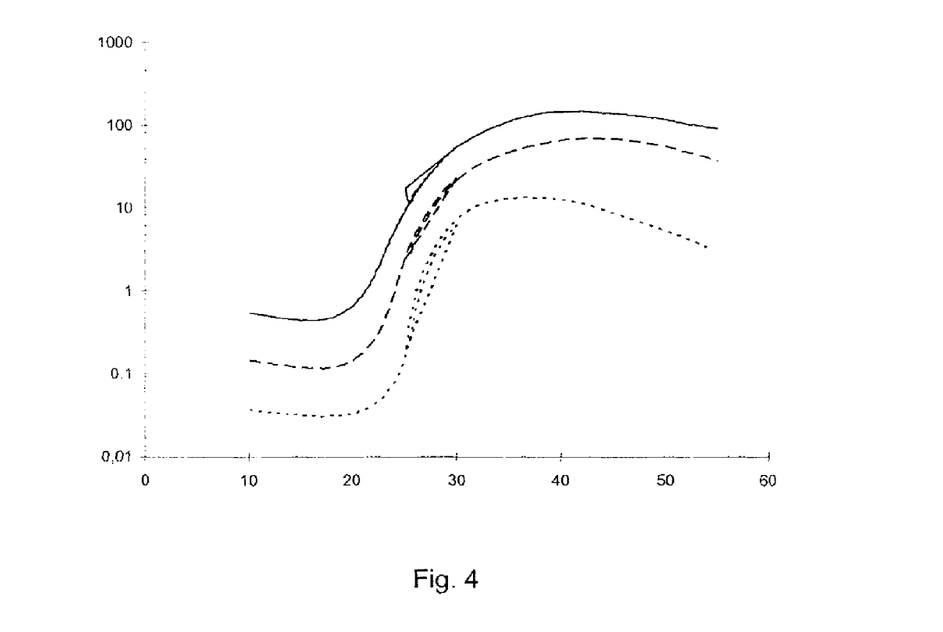

The effect of the polymer concentration on the viscosification of the solution depending on temperature is illustrated in FIG. 4. FIG. 4 illustrates the viscosity (Pa·s) curve versus temperature (° C.) for the CHI-PEOPPO sample with DS$_1$=0.1, under the following operating conditions: shear rate: 1 s$^{-1}$; heating rate: 1° C./min; solvent: AcOH 0.3 M/AcONa 0.05 M.
  Caption of FIG. 4:
  CHI-PEOPPO, Ds$_1$=0.1, 15 g/L, 0.036 monomol/L: solid line (—)
  CHI-PEOPPO DS$_1$=0.1, 10 g/L, 0.024 monomol/L: dashed line ( - - - )
  CHI-PEOPPO DS$_1$=0.1, 5 g/L, 0.012 monomol/L: dotted lines ( . . . )

Regardless of the concentration, the gain in viscosity reaches a factor close to 1,000. The transition temperature remains substantially unchanged.

Figure 5:
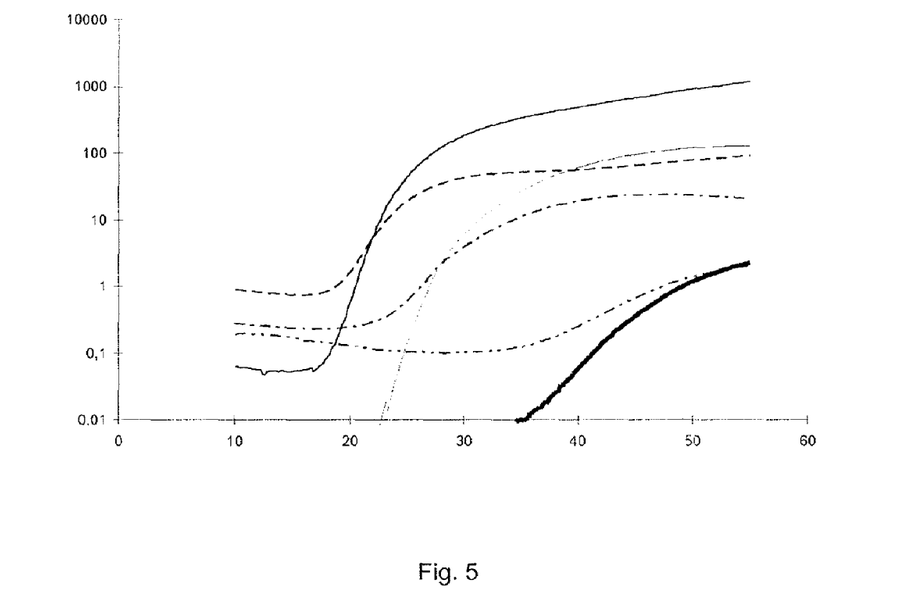

FIG. 5 compares the change in the preservation (elastic) G' and loss (viscous) G" moduli versus temperature for the different CHI-PEOPPO derivatives. The intersection between the preservation modulus G' and the loss modulus G" is located at the critical temperature Tc. This temperature delimits two domains: in the low temperature region (T<Tc) the viscous nature is predominant, in the high temperature region (T>Tc) the elastic nature is predominant. The plotted curves give the variation of the moduli G' and G" (Pa) versus temperature (° C.) for different thermoassociative CHI-PEOPPO copolymers under the following operating conditions: frequency set to 1 Hz; heating rate: 1° C./min; solvent: AcOH 0.3 M/AcONa 0.1 M; Cp=0.024 monomol/L.

Caption of FIG. 5:
G', CHI-PEOPPO $DS_1$=0.1: dotted line ( . . . )
G", CHI-PEOPPO $DS_1$=0.1: dash-dot line (-.-.-.)
G', CHI-PEOPPO $DS_1$=0.17: solid line (—)
G", CHI-PEOPPO $DS_1$=0.17: dashed line ( - - - )
G', CHI-PEOPPO $DS_1$=0.04: bold solid line (━━)
G", CHI-PEOPPO $Ds_1$=0.04: dash-two-dots line (-..-..)

A significant increase in the moduli G' and G" versus temperature is observed for derivatives with higher $DS_1$ ($DS_1$=0.17 and 0.1). At low temperature, the compounds in solution at pH 4 have a behavior of the viscous solution type (G'<G") but above 25° C., they adopt a behavior of the gel type (G'>G"). The thermoassociation phenomenon is therefore well shown for these derivatives.

EXAMPLE 7

Comparison of the Flow Behaviors of CHI-PEOPPO Derivatives and of CHI-PEOPPO-PEO Derivatives in an Aqueous Medium The flow behaviors of CHI-PEOPPO and CHI-PEOPPO-PEO in an aqueous medium were investigated. The operating conditions are the following:
CHI-PEOPPO with $DS_1$ 0.17 in $CH_2COOH$ 0.3 M/$CH_3COONa$ 0.1M (14.9 g/L or 0.024 monomol/L) and
CHI-PEOPPO-PEO ($DS_{PEOPPO}$ ($DS_1$)=0.18 and $DS_{PEO}$ ($DS_2$)=0.28) in a phosphate buffer (pH=7.4, [NaCl]=0.134M) (28.8 g/L or 0.025 monomol/L);
the frequency is set to 1 Hz;
the heating rate is 1° C./min.

Figure 6:
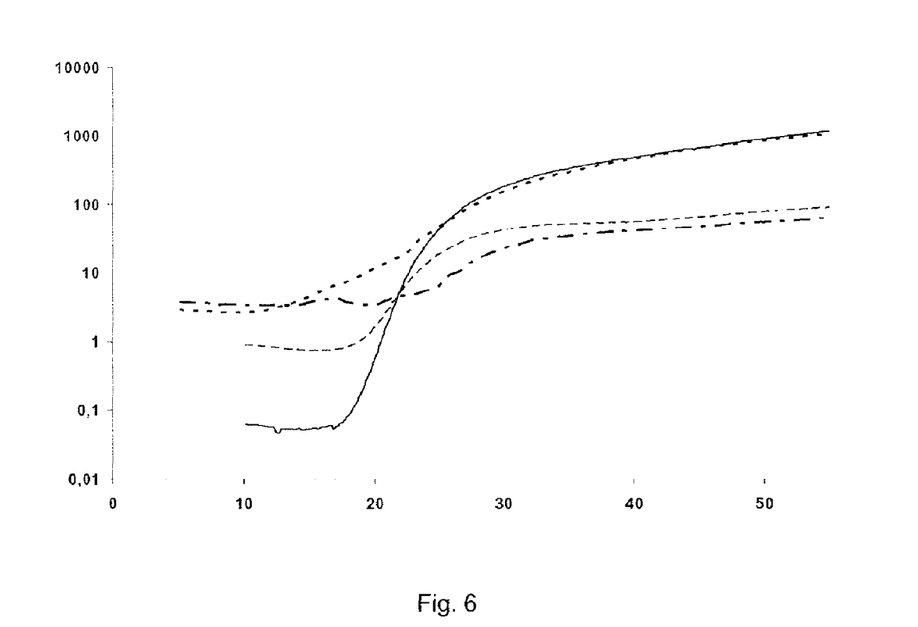

The results are given in FIG. 6 which represents the variation of the G' and G" moduli (Pa) of the aqueous solution versus temperature (° C.). Caption:
G', CHI-PEOPPO $DS_1$=0.17: dotted lines ( . . . )
G", CHI-PEOPPO $DS_1$=0.17: dash-dot line (-.-.-.)
G', CHI-PEOPPO $DS_1$=0.18: solid line (—)
G", CHI-PEOPPO $DS_1$=0.18: dashed line ( - - - )

According to FIG. 6, it may be noted that the moduli G' and G" are higher at low temperatures, in the case of the CHI-PEOPPO-PEO derivative. The thickening effect induced by the presence of PEO groups is also observed when the viscosity of CHI-PEO solutions and that of native chitosan are compared under the same solvent conditions. This difference is enhanced when the CHI-PEO derivative is solubilized, such as in the present case, for the CHI-PEOPPO-PEO derivative, in the phosphate buffer at pH 7.4 (with [NaCl]= 0.134 M), where electrostatic repulsions are considerably reduced, thereby promoting interchain associations. Moreover, it may be noted that the presence of grafted PEO chains causes the presence of the intersection point of the curves G' and G" at a lower temperature, but does not have any significant effect on the value of the modules at high temperatures. These results therefore seem to indicate that during the temperature increase, the PEOPPO grafts aggregate and the presence of PEO chains reinforces the association phenomenon.

Figure 7:
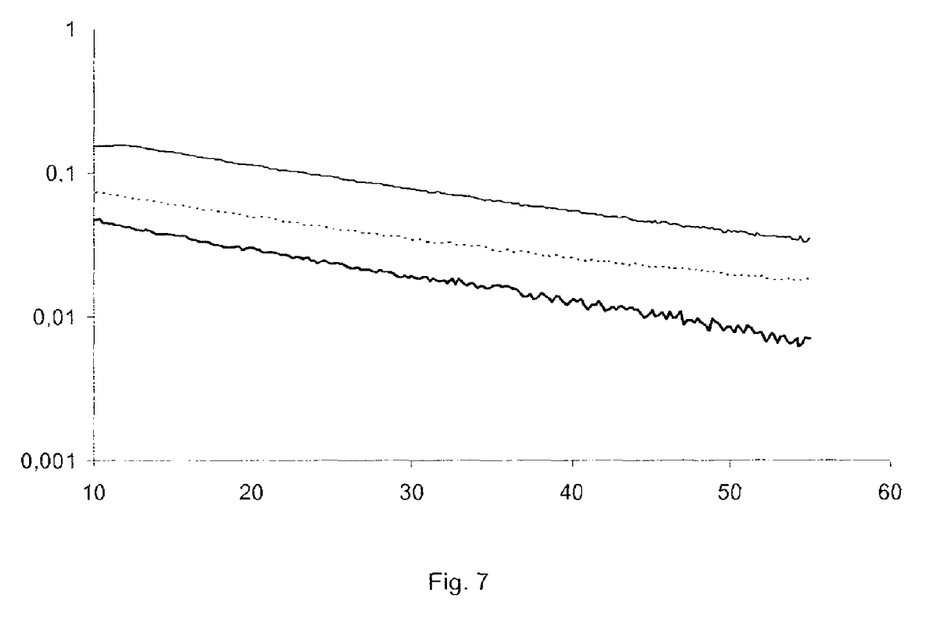

FIG. 7 shows the change in the viscosity versus the shear gradient for a solution of CHI-PEO at 17.7 g/L (0.025 monomol/L) in various solvents and the initial chitosan.

Caption of FIG. 7: viscosity (Pa·s) versus temperature (° C.)
CHI-PEO in PBS—phosphate buffer (pH-7.4, [NaCl]=0.134 M): solid line (━━)
CHI-PEO in acid—AcOH 0.3M/AcONa 0.05M: dotted line ( . . . )
Native CHI in acid—AcOH 0.3M/AcONa 0.05 M: bold solid line (━━)

Higher viscosity values are seen for the CHI-PEO derivative. For this derivative, the use of a phosphate buffer at pH 7.4 (with [NaCl]=0.134M) where electrostatic repulsions are considerably reduced, promotes interchain associations.

The invention claimed is:

1. A method for preparing a thermosensitive poly(ethylene oxide) polypropylene oxide)-acetal (PEOPPO-acetal) compound comprising the following successive steps:
   a. reaction of one or more random polyetheramines of generic formula (I)

wherein p represents an integer varying from 1 to 40, and m represents an integer varying from 1 to 40, with succinic anhydride in order to lead to the corresponding acid; and
   b. coupling of the acid obtained following step a) with 2,2-dimethoxyethylamine in order to lead to the PEOPPO-acetal compound.

2. The preparation method according to claim 1, wherein the reaction of step (a) is carried out in anhydrous DMF.

3. The preparation method according to claim 1, wherein following step a) and prior to step b), the reaction medium is left under stirring.

4. The preparation method according to claim 1, wherein the reaction of step b) is carried out in DMF.

5. The preparation method according to claim 1, wherein step b) further comprises the addition of 1-ethyl-3-[3-(dimethylamino)propyl]-carbodiimide and diisopropylamine in the coupling reaction.

6. The preparation method according to claim 1, wherein the steps a) and b) are carried out in a single pot.

7. A PEOPPO-acetal compound obtained by the method according to claim 1.

8. A method for the synthesis of grafted chitosan comprising (i) hydrolyzing a PEOPPO-acetal compound into a PEOPPO-aldehyde (PEOPPO-CHO) compound followed by (ii) grafting said PEOPPO-CHO compound on chitosan or one of its derivatives (CHI) by a reaction of the reducing amination type to form CHI-PEOPPO,
   wherein said chitosan or one of its derivatives has the following formula (II):

wherein n varies from 60 to 6,000 and R represents
      a hydrogen atom H, or
      an acetyl radical $COCH_3$ wherein the PEOPPO-acetal compound is obtainable by a method comprising the following successive steps:
a. reaction of one or more random polyetheramines of generic formula (I)

(I)

wherein p represents an integer varying from 1 to 40 and m represents an integer varying from 1 to 40, with succinic anhydride in order to lead to the corresponding acid; and
b. coupling of the acid obtained following step a) with 2,2-dimethoxyethylamine in order to lead to the PEOPPO-acetal compound.

9. The method according to claim 8, wherein p represents an integer varying from 3 to 29.

10. The method according to claim 8, wherein m represents an integer varying from 1 to 31.

11. The method according to claim 8, wherein the reaction of step (a) is carried out in anhydrous DMF.

12. The method according to claim 8, wherein following step a) and prior to step b), the reaction medium is left under stirring.

13. The method according to claim 8, wherein the reaction of step b) is carried out in DMF.

14. The method according to claim 8, wherein step b) further comprises the addition of 1-ethyl-3-[3-(dimethylamino)propyl]-carbodiimide and diisopropylamine in the coupling reaction.

15. The method according to claim 8, wherein the steps a) and b) are carried out in a single pot.

16. The method according to claim 8, wherein the acetylation degree of said chitosan or one of its derivatives is between 0 and 0.5.

17. The method according to claim 16, wherein the acetylation degree is between 0 and 0.2.

18. The method according to claim 8, further comprising (iii) functionalizing the CHI-PEOPPO with a polymer.

19. The method according to claim 18, wherein the CHI-PEOPPO is functionalized by a poly(ethylene oxide) having a degree of substitution greater than 0.1.

20. The method according to claim 19, wherein the poly(ethylene oxide) has a molecular mass between 1,000 and 5,000 g/mol.

21. A CHI-PEOPPO-PEO compound obtainable by a method according to claim 18.

22. An aqueous composition comprising at least one CHI-PEOPPO-PEO compound according to claim 21 and an aqueous phase.

23. The aqueous composition according to claim 22, wherein the CHI-PEOPPO-PEO compound is present in an amount between 2 and 30 g/L.

24. The aqueous composition according to claim 22, wherein the pH of said aqueous composition varies from 4 to the physiological pH.

25. The aqueous composition according to claim 22, further comprising a cosmetically or pharmaceutically acceptable medium.

26. A method for making a gel, comprising heating the aqueous composition according to claim 22.

* * * * *